United States Patent
Ihara (10) Patent No.: US 9,754,368 B2
(45) Date of Patent: Sep. 5, 2017

(54) REGION EXTRACTION APPARATUS, METHOD, AND PROGRAM

(71) Applicant: FUJIFILM Corporation, Tokyo (JP)

(72) Inventor: Satoshi Ihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/867,210

(22) Filed: Sep. 28, 2015

(65) Prior Publication Data
US 2016/0019694 A1 Jan. 21, 2016

Related U.S. Application Data

(63) Continuation of application No. PCT/JP2014/001802, filed on Mar. 27, 2014.

(30) Foreign Application Priority Data

Mar. 29, 2013 (JP) ................. 2013-073886

(51) Int. Cl.
*G06K 9/00* (2006.01)
*G06T 7/00* (2017.01)
(Continued)

(52) U.S. Cl.
CPC .......... *G06T 7/0012* (2013.01); *G06K 9/4604* (2013.01); *G06T 5/30* (2013.01);
(Continued)

(58) Field of Classification Search
None
See application file for complete search history.

(56) References Cited

U.S. PATENT DOCUMENTS 5,661,818 A * 8/1997 Gaborski ........... G06K 9/00449
378/164
5,668,888 A * 9/1997 Doi ........................ G06T 5/50
382/132
(Continued)

FOREIGN PATENT DOCUMENTS

CN 101295404 A 10/2008
EP 2 068 281 A1 6/2009
(Continued)

OTHER PUBLICATIONS

Illingworth et al ("A survey of the Hough Transform", 1988).*
(Continued)

*Primary Examiner* — Avinash Yentrapati
(74) *Attorney, Agent, or Firm* — Sughrue Mion, PLLC (57) ABSTRACT

An apparatus includes a gaseous region extraction unit that extracts a gaseous region from a lumen image, a residue candidate region extraction unit that extracts a candidate of a residue region from the lumen image as a residue candidate region, a boundary candidate region detection unit that detects a boundary candidate region that includes a boundary between the gaseous region and the residue candidate region, a representative direction component obtaining unit that obtains a representative direction component representing a plurality of directional components of an image in the boundary candidate region, a boundary region detection unit that detects a boundary region that includes a boundary between the gaseous region and the residue region from the boundary candidate regions based on the representative direction component, and a residue region extraction unit that extracts the residue candidate region that includes the boundary region as the residue region.

15 Claims, 6 Drawing Sheets

(51) Int. Cl.
  *G06K 9/46* (2006.01)
  *G06T 5/30* (2006.01)
  *G06T 7/12* (2017.01)
  *A61B 6/03* (2006.01)
(52) U.S. Cl.
  CPC ............... *G06T 7/12* (2017.01); *A61B 6/032* (2013.01); *G06T 2207/10004* (2013.01); *G06T 2207/10081* (2013.01); *G06T 2207/30028* (2013.01)

(56) References Cited

U.S. PATENT DOCUMENTS

| | | | | | |
|---|---|---|---|---|---|
| 5,960,371 | A * | 9/1999 | Saito | ........................ | G01V 1/50 702/10 |
| 6,331,116 | B1 * | 12/2001 | Kaufman | ............... | G06K 9/209 345/418 |
| 6,514,082 | B2 * | 2/2003 | Kaufman | ............... | G06K 9/209 345/418 |
| 7,574,024 | B2 * | 8/2009 | Bitter | ........................ | G06T 7/64 382/128 |
| 7,596,256 | B1 * | 9/2009 | Arie | ...................... | G06T 7/0012 382/128 |
| 2002/0097320 | A1 * | 7/2002 | Zalis | ........................ | G06T 5/50 348/65 |
| 2004/0101181 | A1 * | 5/2004 | Giger | .................... | G06T 7/0012 382/128 |
| 2004/0161141 | A1 * | 8/2004 | Dewaele | .............. | G06K 9/3208 382/132 |
| 2006/0157069 | A1 * | 7/2006 | Matsumoto | ............ | A61B 6/032 128/898 |
| 2007/0073114 | A1 * | 3/2007 | Gundel | .................. | A61K 49/04 600/300 |
| 2008/0008367 | A1 * | 1/2008 | Franaszek | ................ | G06K 9/34 382/128 |
| 2008/0027315 | A1 * | 1/2008 | McGinnis | ............. | G06T 7/0012 600/425 |
| 2009/0304248 | A1 | 12/2009 | Zalis et al. | | |
| 2010/0128036 | A1 * | 5/2010 | Johnson | .................... | G06T 5/50 345/424 |
| 2011/0013815 | A1 * | 1/2011 | Gundel | .................. | A61B 5/055 382/128 |
| 2013/0208958 | A1 * | 8/2013 | Tomoto | .............. | A61B 1/00009 382/128 |
| 2013/0304446 | A1 * | 11/2013 | Rabinovitz | ............. | G06F 19/12 703/11 |
| 2013/0308851 | A1 * | 11/2013 | Bertens | ..................... | G06T 7/11 382/132 |
| 2015/0055837 | A1 * | 2/2015 | Rhoads | ................. | G06T 7/0012 382/128 |

FOREIGN PATENT DOCUMENTS

| | | |
|---|---|---|
| JP | 2006-198059 A | 8/2006 |
| JP | 2009-511216 A | 3/2009 |
| JP | 2011-135936 A | 7/2011 |
| WO | 2009/144290 A1 | 12/2009 |

OTHER PUBLICATIONS

Fernandes et al ("Real-time line detection through an improved Hough transform voting scheme", 2006).*

Iwo Serlie et al., Computed Cleansing for Virtual Colonoscopy Using a Three-Material Transition Model, Medical Image Computing and Computer-Assisted Intervention, Lecture Notes in Computer Science, 2003, pp. 175-183, vol. 2879.

Yasunori Wakamatsu et al., "Extraction Method of Intestinal Wall Using Gradient of CT Value for Virtual Colonoscopy", IEICE Technical Report, Jan. 21, 2010, pp. 447-451, vol. 109, No. 407.

Takashi Adachi et al., "CT Colonography using the stool tagging method", IEICE Technical Report, Jan. 20, 2006, pp. 53-56, vol. 105, No. 579.

International Search Report for PCT/JP2014/001802 dated Jun. 10, 2014.

Written Opinion for PCT/JP2014/001802 dated Jun. 10, 2014.

* cited by examiner

Sobel FILTER (Z DIRECTION)

FIG.7

EXAMPLE OF VOTING RESULT

REGION EXTRACTION APPARATUS, METHOD, AND PROGRAM

CROSS-REFERENCE TO RELATED APPLICATIONS

This application is a Continuation of PCT International Application No. PCT/JP2014/001802 filed on Mar. 27, 2014, which claims priority under 35 U.S.C. §119 (a) to Japanese Patent Application No. 2013-073886 filed on Mar. 29, 2013. Each of the above applications is hereby expressly incorporated by reference, in its entirety, into the present application.

BACKGROUND

The present disclosure relates to a region extraction processing apparatus, method, and program for extracting, from a lumen image which includes a hollow organ, a residue region in the hollow organ.

Recently, it has been practiced to extract a hollow organ, such as a large intestine, a small intestine, a stomach, from a three-dimensional image captured by a modality, such as a computed tomography (CT) system, and to use the three-dimensional image of the extracted hollow organ for image diagnosis.

For example, it is possible to create an image as if observing by an endoscope by CT imaging a large intestine with the air in the large intestine, and volume rendering the three-dimensional image captured by the CT imaging from inside the large intestine, and such image is called a virtual endoscopic image.

When generating the virtual endoscopic image, it is necessary to extract the large intestine from the three-dimensional image. It is also necessary to empty the inside of the large intestine before examination, but sometimes a residue may remain in the large intestine. The residue remaining in the virtual endoscopic image may hinder the observation of inside the large intestine.

Figure 10:
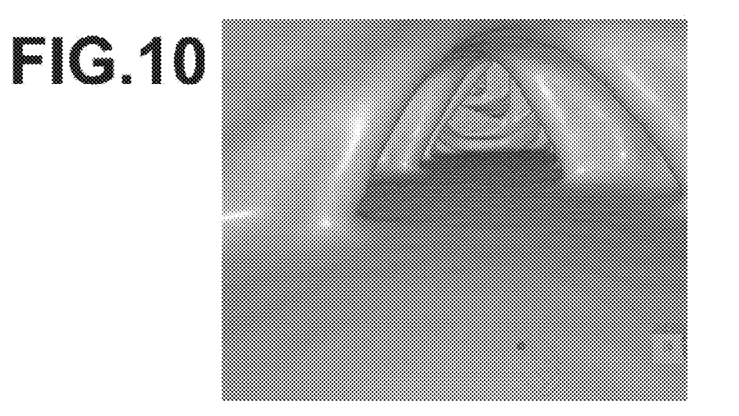
FIG. 10 shows an example of a virtual endoscopic image before digital cleansing.
Figure 11:
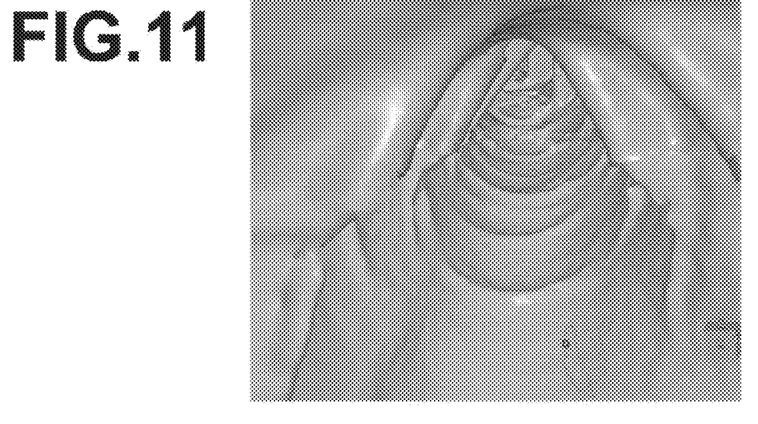
FIG. 11 shows an example of a virtual endoscopic image after digital cleansing.

Hence, the volume rendering may sometimes be performed by virtually generating a three-dimensional image without any residue by contrasting and imaging a residue in advance and eliminating the residue region by image processing after the CT imaging, and such processing is called as a digital cleansing. FIG. 10 shows an example of a virtual endoscopic image generated using a three-dimensional image before being subjected to the digital cleansing, while FIG. 11 shows an example of a virtual endoscopic image generated using a three-dimensional image after being subjected to the digital cleansing.

Figure 12:
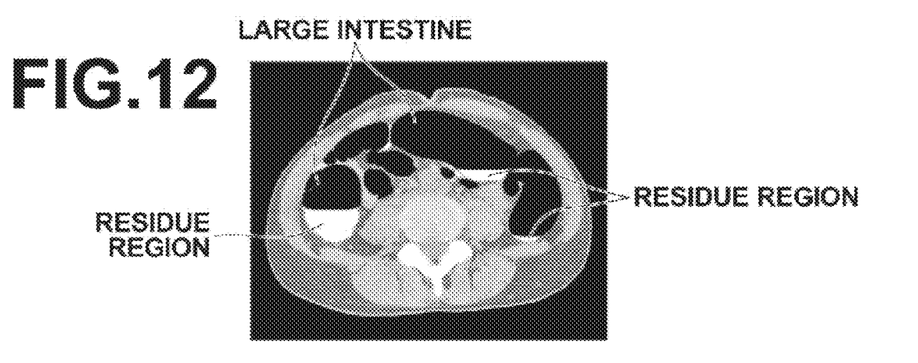
FIG. 12 shows an example of contrasted residue regions in a large intestine.

It is necessary to appropriately extract contrasted residue regions, as shown in FIG. 12, to perform the digital cleansing described above.

Japanese Unexamined Patent Publication No. 2006-198059 proposes a method that uses the fact that a boundary between the large intestine region (air region) and the residue region is horizontal and a region including the horizontal area is extracted as the residue region.

SUMMARY

As the method described in Japanese Unexamined Patent Publication No. 2006-198059 is based on the assumption that the liquid surface of a residue is horizontal, however, if an image obtained by CT-imaging in a prone position is displayed upside down, a residue region may not be extracted appropriately since the liquid surface is not necessarily horizontal. Further, in a case where the residue region is a relatively small region, it is very difficult to determine whether or not the liquid surface is a horizontal plane, as the liquid surface is small.

Figure 13:
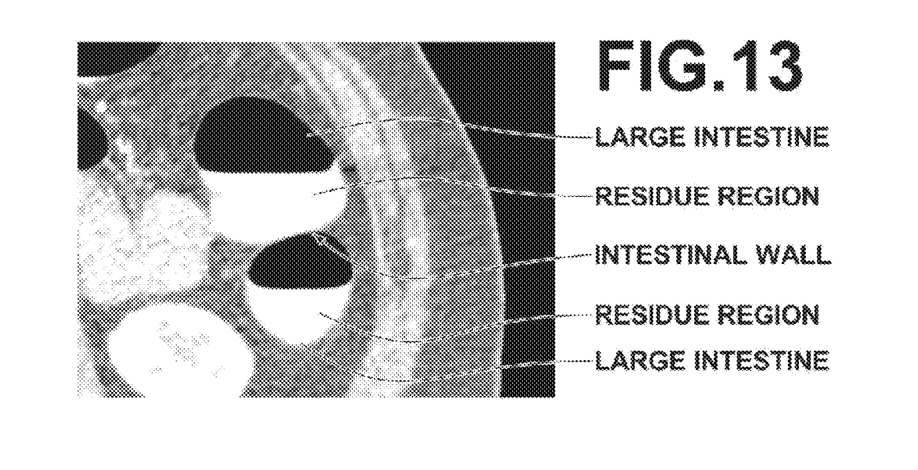
FIG. 13 shows a state in which portions of a large intestine are in contact with each other and residues are accumulated on one side.

Further, for example, in a case where portions of a large intestine are in contact with each other and residues are accumulate on one side, as shown in FIG. 13, the area where the portions of the large intestine are in contact with each other is a plane relatively horizontal so that an intestinal wall portion may also be erroneously detected as a residue region. Such an erroneous detection may cause the intestinal wall of the large intestine to be eliminated during the digital cleansing, whereby a virtual endoscopic image with a hole may be generated.

In view of the circumstances described above, the present disclosure provides a region extraction processing apparatus, method, and program capable of extracting, from a lumen image containing a hollow organ, such as a large intestine, a residue region in the hollow organ with high accuracy.

A region extraction processing apparatus of the present disclosure includes a gaseous region extraction unit that extracts a gaseous region from a lumen image that includes a hollow organ, a residue candidate region extraction unit that extracts a candidate of a residue region in the hollow organ from the lumen image as a residue candidate region, a boundary candidate region detection unit that detects a boundary candidate region that includes a boundary between the gaseous region and the residue candidate region, a representative direction component obtaining unit that obtains a representative direction component representing a plurality of directional components of an image in the boundary candidate region, a boundary region detection unit that detects a boundary region that includes a boundary between the gaseous region and the residue region from the boundary candidate regions based on the representative direction component, and a residue region extraction unit that extracts the residue candidate region that includes the boundary region as the residue region.

In the region extraction processing apparatus of the present disclosure described above, the boundary candidate region detection unit may dilate each of the gaseous region and the residue candidate region and may detect a region common to the gaseous region and the residue candidate region after the dilation as the boundary candidate region.

Further, the representative direction component obtained unit may obtain the representative direction component by performing a voting process on the plurality of directional components.

Still further, the representative direction obtaining unit may perform a voting on values obtained by polar coordinate transformation of the directional components and may obtain a directional component having a maximum peak in the polar coordinate space as the representative directional component, and the boundary region detection unit may detect the boundary candidate region that includes the representative directional component as the boundary region.

As a result of the voting, if the maximum peak is less than a predetermined threshold value, the detection of the boundary region in the boundary region detection unit and the extraction of the residue region in the residue region extraction unit may not be performed.

Further, the representative direction component obtaining unit may calculate a normal direction component of each pixel in the boundary candidate region and may obtain the representative direction component based on the normal direction component.

Still further, the representative direction component obtaining unit may calculate the normal direction component of each pixel based on a density gradient in the boundary candidate region.

Further, the representative direction component obtaining unit may calculate the density gradient using a Sobel filter.

Still further, the residue candidate region extraction unit may extract a bone region or a contrasted blood vessel region along with the residue region as the residue candidate region.

Further, the hollow organ may be a large intestine.

Still further, the lumen image may be a three-dimensional image.

A region extraction processing method of the present disclosure includes the steps of extracting a gaseous region from a lumen image that includes a hollow organ, extracting a candidate of a residue region in the hollow organ from the lumen image as a residue candidate region, detecting a boundary candidate region that includes a boundary between the gaseous region and the residue candidate region, obtaining a representative direction component representing a plurality of directional components of an image in the boundary candidate region, and detecting a boundary region that includes a boundary between the gaseous region and the residue region from the boundary candidate regions based on the representative direction component, and extracting the residue candidate region that includes the boundary region as the residue region.

A region extraction processing program of the present disclosure causes a computer to function as a gaseous region extraction unit that extracts a gaseous region from a lumen image that includes a hollow organ, a residue candidate region extraction unit that extracts a candidate of a residue region in the hollow organ from the lumen image as a residue candidate region, a boundary candidate region detection unit that detects a boundary candidate region that includes a boundary between the gaseous region and the residue candidate region, a representative direction component obtaining unit that obtains a representative direction component representing a plurality of directional components of an image in the boundary candidate region, a boundary region detection unit that detects a boundary region that includes a boundary between the gaseous region and the residue region from the boundary candidate regions based on the representative direction component, and a residue region extraction unit that extracts the residue candidate region that includes the boundary region as the residue region.

According to the region extraction processing apparatus, method, and program of the present disclosure, a gaseous region is extracted from a lumen image that includes a hollow organ, a candidate of a residue region in the hollow organ is extracted from the lumen image as a residue candidate region, a boundary candidate region that includes a boundary between the gaseous region and the residue candidate region is detected, a representative direction component representing a plurality of directional components of an image in the boundary candidate region is obtained, and a boundary region that includes a boundary between the gaseous region and the residue region is detected from the boundary candidate regions based on the representative direction component, and the residue candidate region that includes the boundary region is extracted as the residue region. This allows the residue region with high accuracy. The advantageous effects of the present disclosure will be described in detail later.

DETAILED DESCRIPTION OF THE PREFERRED EMBODIMENTS

Figure 1:
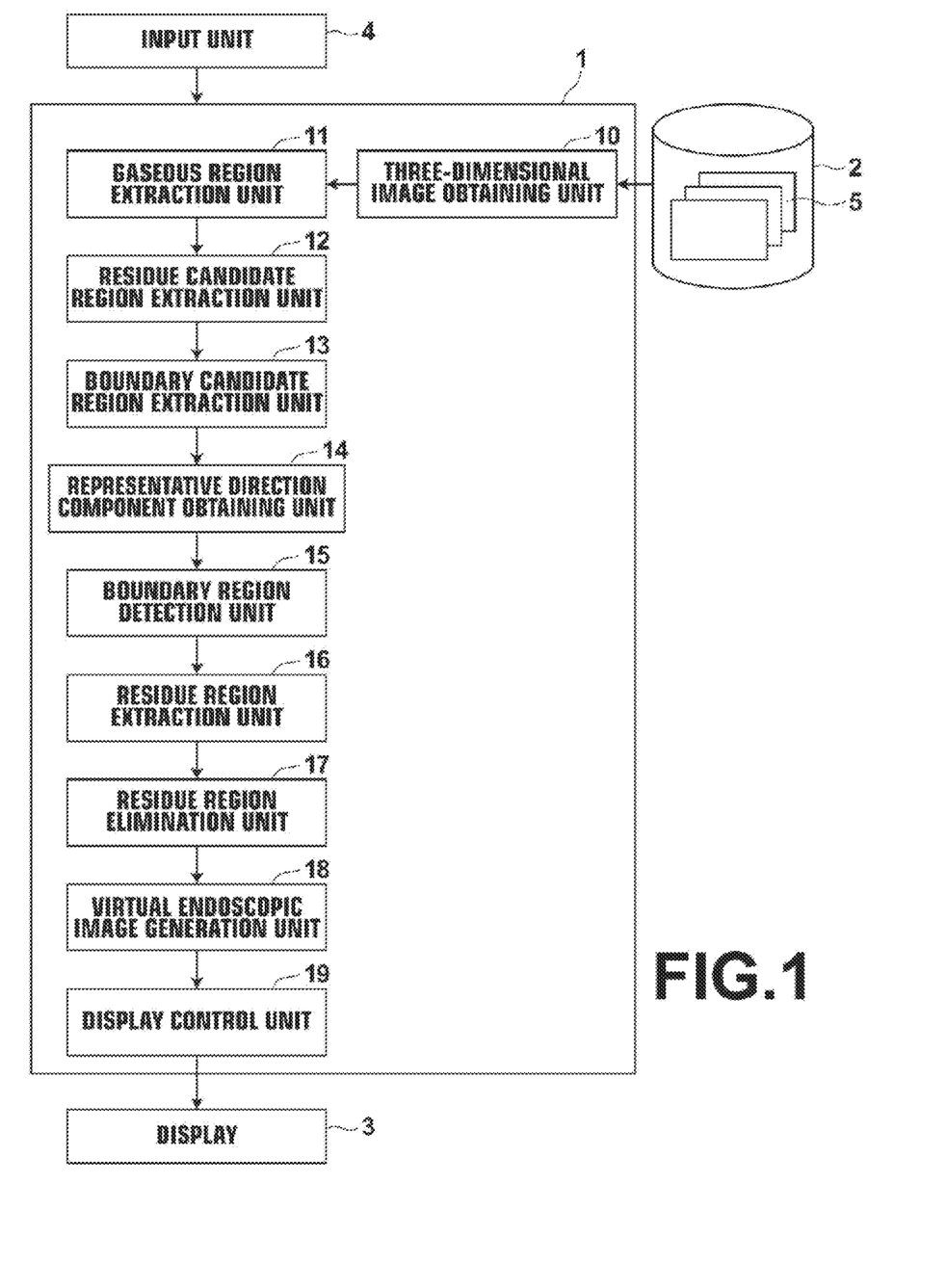
FIG. 1 is a block diagram of a medical image diagnosis support system that uses one embodiment of the region extraction processing apparatus, method, and program of the present disclosure, schematically illustrating the configuration thereof.

Hereinafter, a medical image diagnosis support system that uses one embodiment of the region extraction processing apparatus, method, and program of the present disclosure will be described in detail with reference to the accompanying drawings. FIG. 1 is a block diagram of the medical image diagnosis support system of the present embodiment.

As illustrated in FIG. 1, the medical image diagnosis support system of the present embodiment includes a medical image display control apparatus 1, a three-dimensional image storage server 2, a display 3, and an input unit 4.

The medical image display control apparatus 1 is a computer on which the medical image display control program of the present embodiment is installed. The medical image display control apparatus 1 includes one embodiment of the region extraction processing apparatus of the present disclosure.

The medical image display control apparatus 1 includes a central processing unit (CPU) and storage devices, such as a semiconductor memory, a hard disk, a solid state drive (SSD), and the like. The storage device includes a medical image display control program that includes a region extraction processing program of the present embodiment, and execution of the medical image display control program by the central processing unit causes a three-dimensional image obtaining unit 10, a gaseous region extraction unit 11, a residue candidate region extraction unit 12, a boundary candidate region detection unit 13, a representative direction component obtaining unit 14, a boundary region detection unit 15, a residue region extraction unit 16, a residue region elimination unit 17, a virtual endoscopic image generation unit 18, and a display control unit 19, as shown in FIG. 1, to be operated.

The three-dimensional image obtaining unit 10 obtains a three-dimensional image 5 of a subject captured in advance before surgery or examination. The three-dimensional image 5 may be, for example, volume data reconstructed from slice data outputted from a computed tomography (CT) system, a magnetic resonance imaging (MRI) system, an ultrasonic imaging system, or the like. The three-dimensional image 5 is stored in the three-dimensional image storage server 2 in advance with identification information of the subject, and the three-dimensional image obtaining unit 10 reads out a three-dimensional image 5 corresponding to the identification information inputted at the input unit 4 from the three-dimensional image storage server 2. Note that volume data may be generated in the three-dimensional image obtaining unit 10 by obtaining a multitude of slice data.

The three-dimensional image obtaining unit 10 according to the present embodiment is assumed to obtain a three-dimensional image that includes a large intestine obtained by a CT system. Note that, however, the three-dimensional image obtaining unit 10 is not limited to obtain a three-dimensional image that includes a large intestine and may obtain a three-dimensional image that includes other hollow organs in which residues may possibly present, such as a stomach, a small intestine, or the like.

The gaseous region extraction unit 11 receives the three-dimensional image 5 obtained by the three-dimensional image obtaining unit 10 and extracts a gaseous region included in the inputted three-dimensional image 5. In the present embodiment, an air region is extracted as the gaseous region.

More specifically, the gaseous region extraction unit 11 extracts a region having a CT value less than or equal to −800 from the three-dimensional image 5. The extracted air region substantially represents the large intestine region. The extraction of the air region by the threshold judgement of CT values described above may sometimes result in that a small intestine, a stomach, and a lung, are also extracted other than the large intestine, but these regions will be excluded from the target of residue region extraction processing by the subsequent processing, so that there is no particular problem. Note that, in a case where another gas is filled in the large intestine, the gas region may be extracted.

The residue candidate region extraction unit 12 receives the three-dimensional image 5 obtained by the three-dimensional image obtaining unit 10, and extracts a residue candidate region included in the inputted three-dimensional image 5.

More specifically, the residue candidate region extraction unit 12 extracts a region having a. CT value greater than or equal to 120. The extraction of the residue candidate region by the threshold judgement of CT values described above may sometimes result in that a bone region and a contrasted blood vessel region are also extracted other than the residue region at the same time. That is, in the present embodiment, regions having a CT value close to the CT value of the residue, such as a bone or a contrasted blood vessel, are also extracted as residue candidate regions. But, the bone and contrasted blood vessel regions will be excluded from the residue region by the subsequent processing, so that there is no particular problem.

The boundary candidate detection unit 13 detects, based on the air region extracted by the gaseous region extraction unit 11 and the residue candidate region extracted by the residue candidate region extraction unit 12, a boundary candidate region that includes a boundary of these regions.

More specifically, the boundary candidate detection unit 13 dilates the air region extracted by the gaseous region extraction unit 11 and the residue candidate region extracted by the residue candidate region extraction unit 12, and detects a region common to the air region and residue candidate region after the dilation as a boundary candidate region. Note that the method of detecting the boundary candidate region is not limited to the method described above, and the other processing may be used as long as it is processing to detect a region that includes the boundary between the air region and the residue candidate region.

The representative direction component obtaining unit 14 performs voting on directional components of the image within the boundary candidate region detected by the boundary candidate region detection unit 13 and obtains a representative direction component based on the result of the voting. The vote processing in the representative direction component obtaining unit 14 will be described in detail later.

The boundary region detection unit 15 detects a boundary region that includes a boundary between the gaseous region and the residue region based on the representative direction component obtained by the representative direction component obtaining unit 15. The boundary region detection processing will also be described in detail later.

The residue region extraction unit 16 detects the residue region based on the boundary region detected by the boundary region detection unit 15. More specifically, the residue region extraction unit 16 detects the residue candidate region that includes the boundary region detected by the boundary region detection unit 15 as the final residue region. That may exclude the regions of a bone and a contrasted blood vessel included in the residue candidate regions.

The residue region elimination unit 17 eliminates the residue region extracted by the residue region extraction unit 16 from the three-dimensional image 5. That is, the residue region elimination unit 17 performs the so-called digital cleansing.

The virtual endoscopic image generation unit 18 generates a virtual endoscopic image based on the three-dimensional image 5 subjected to the digital cleansing in the residue region elimination unit 17.

More specifically, the virtual endoscopic image generation unit 18 generates an image, as the virtual endoscopic image, by central projection method in which voxel data in a plurality of light ray directions extending radially centered on a visual line vector, which bases on a predetermined viewpoint and a visual line direction, are projected on a given projection plane. Specific central projection methods that can be used include, for example, the known volume rendering method and the like.

The display control unit 19 displays the virtual endoscopic image generated by the virtual endoscopic image generation unit 18 on the display 3.

The input unit 4 includes a mouse, a keyboard, and the like, and receives an operation input by the user. For example, the input unit 4 receives a setting input of the viewpoint and visual line direction used when generating the virtual endoscopic image, as described above.

Figure 2:
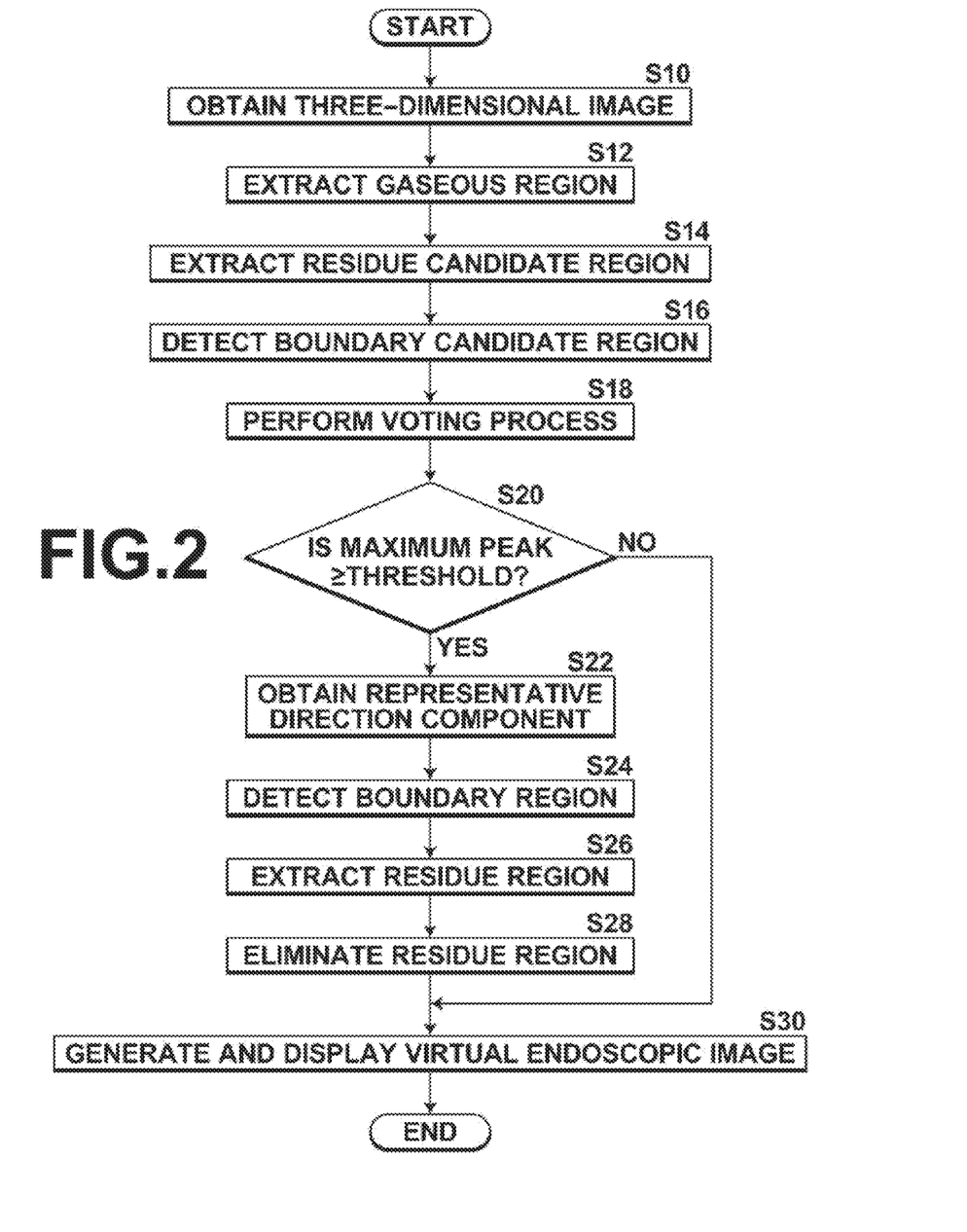
FIG. 2 is a flowchart for explaining an operation of the medical image diagnosis support system illustrated in FIG. 1.

An operation of the medical image diagnosis support system of the present embodiment will now be described with reference to the flowchart shown in FIG. 2.

First, identification information of a subject is inputted by the user using the input unit 4, and the three-dimensional image obtaining unit 10 of the medical image display control apparatus 1 reads out and obtains a three-dimensional image 5 corresponding to the inputted identification information of the subject from the three-dimensional image storage server 2 (S10).

The three-dimensional image 5 obtained by the three-dimensional image obtaining unit 10 is inputted to the gaseous region extraction unit 11, and the gaseous region extraction unit 11 extracts an air region from the inputted three-dimensional image 5 (S12).

The three-dimensional image 5 obtained by the three-dimensional image obtaining unit 10 is also inputted to the residue candidate region extraction unit 12, and the residue candidate region extraction unit 12 extracts a residue candidate region from the inputted three-dimensional image 5 (S14).

Then, information of the air region extracted by the gaseous region extraction unit 11 and information of the residue candidate region extracted by the residue candidate region extraction unit 12 are inputted to the boundary candidate detection unit 13, and the boundary candidate detection unit 13 detects a boundary candidate region based on these information (S16). More specifically, the boundary candidate detection unit 13 dilates the air region and the residue candidate region, and detects a region common to the air region and residue candidate region after the dilation as a boundary candidate region, as described above.

Figure 3:
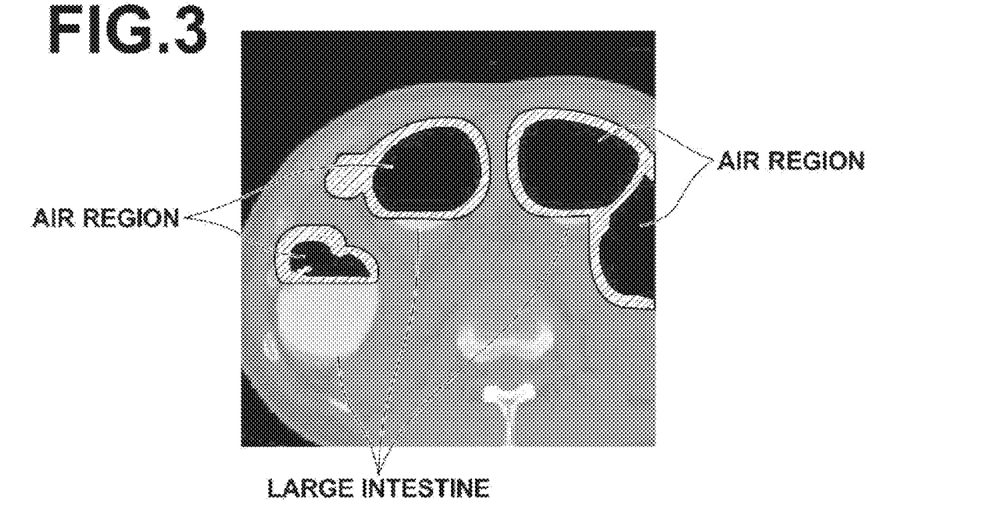
FIG. 3 shows an example of air regions after dilation.
Figure 4:
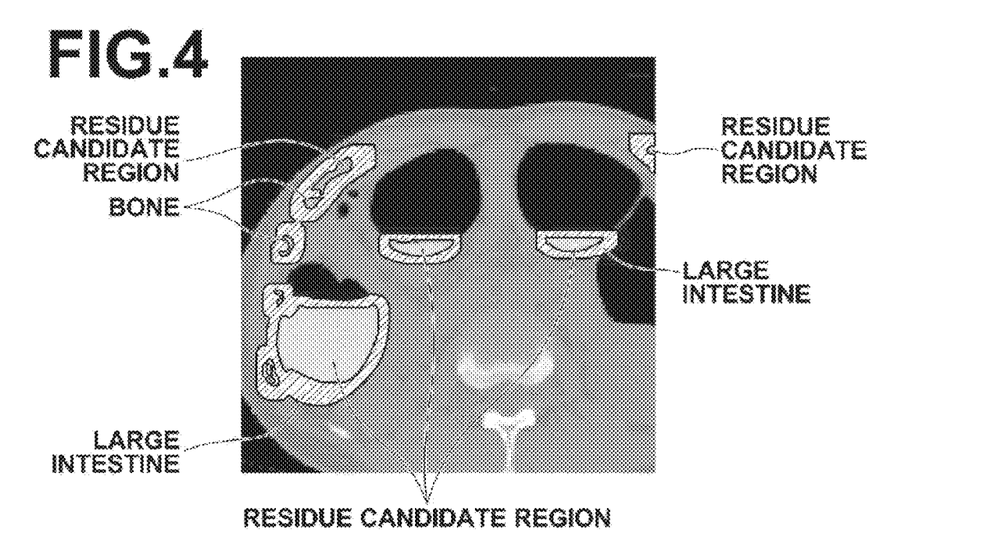
FIG. 4 shows an example of residue candidate regions after dilation.

FIG. 3 shows an example of an air region after dilation, and the hatched region in FIG. 3 is a dilated region of the air region. FIG. 4 shows an example of a residue candidate region after dilation, and the shaded region in FIG. 4 is a dilated region of the residue candidate region. For the sake of clarity, slice images are shown here, instead of three-dimensional images.

Figure 5:
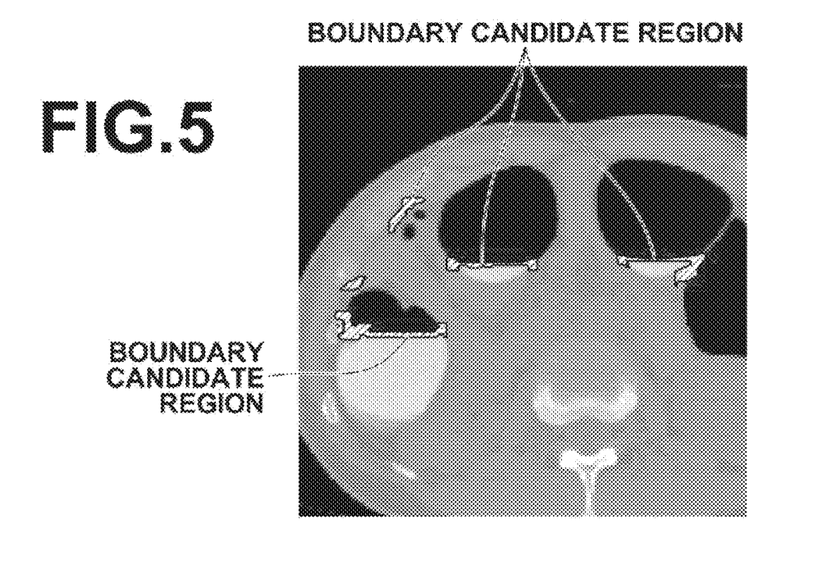
FIG. 5 shows boundary candidate regions which are common to the regions in which the air regions are dilated shown in FIG. 3 and regions in which the residue regions are dilated shown in FIG. 4.

As shown in FIG. 4, residue candidate regions include bone regions around the large intestine as well as residue regions in the large intestine. FIG. 5 shows boundary candidate regions (hatched regions in FIG. 5) which are common regions between the dilated regions of the air regions shown in FIG. 3 and the dilated regions of the residue candidate regions shown in FIG. 4. As shown in FIG. 5, the boundary candidate regions include not only the boundary regions between the residue regions in the large intestine and the air regions, but also a boundary region between a bone region around the large intestine and an air region.

Figure 6:
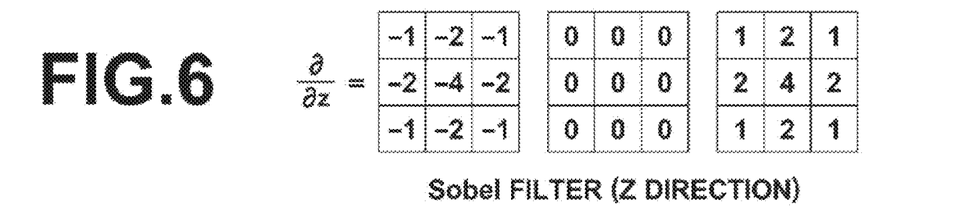
FIG. 6 shows an example of a Sobel filter.

Then, the information of the boundary candidate region detected by the boundary candidate region detection unit 13 is outputted to the representative direction component obtaining unit 14. The representative direction component obtaining unit 14 calculates directional components of each voxel (pixel) of the boundary candidate region and performs voting on the values obtained through polar coordinate transformation of the directional components (S18). More specifically, the representative direction component obtaining unit 14 calculates the density gradient of the image in the boundary candidate region using a Sobel filter, as shown in FIG. 6, and calculates the normal direction of each voxel based on the density gradient. Then, the representative direction component obtaining unit 14 performs polar coordinate transformation on the normal direction of each voxel and performs voting on each polar-coordinate transformed value.

Figure 7:
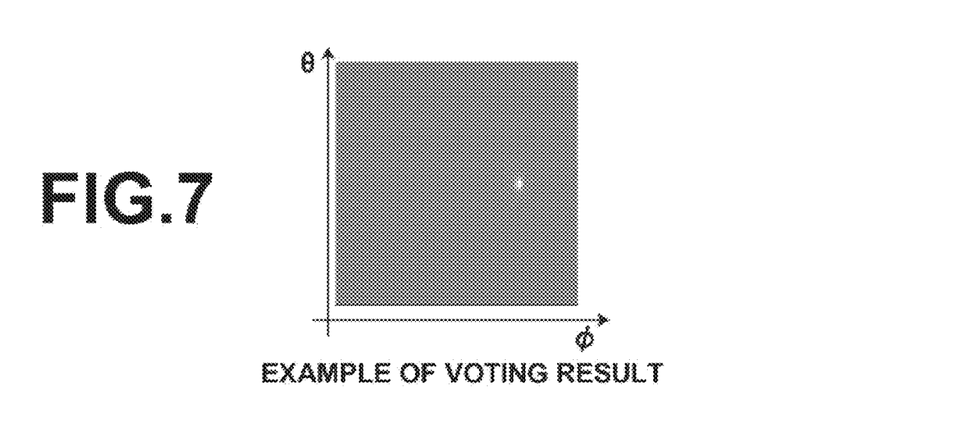
FIG. 7 shows an example of a voting result of the values obtained through polar coordinate transformation of a component in the normal direction of each voxel in a boundary candidate region.

FIG. 7 shows an example of a voting result of each polar-coordinate transformed value. In FIG. 7, voxels are shown more whitish as the number of votes increases. As the normal directions of the voxels in the boundary region between the air region and the residue region are the same, if a residue region is present, a large peak appears at one point, as shown in FIG. 7.

Then, the representative direction component obtaining unit 14 confirms whether or not the maximum peak in the polar coordinate space is greater than or equal to a preset threshold value (S20). If the maximum peak in the polar coordinate space is greater than or equal to a preset threshold value (S20, YES), the representative direction component obtaining unit 14 determines that a residue reason is present, and obtains the normal direction component, which is the maximum peak, as the representative direction component (S22). Then, the representative direction component obtaining unit 14 outputs information of the representative direction component to the boundary region detection unit 15.

Based on the representative direction component, the boundary region detection unit 15 detects a boundary region that includes the boundary between the air region and the residue region from the boundary candidate regions shown in FIG. 5 (S24). More specifically, the boundary region detection unit 15 identifies a voxel having the representative direction component from the voxels in the residue candidate region, and detects a group of the identified voxels as the boundary region.

Figure 8:
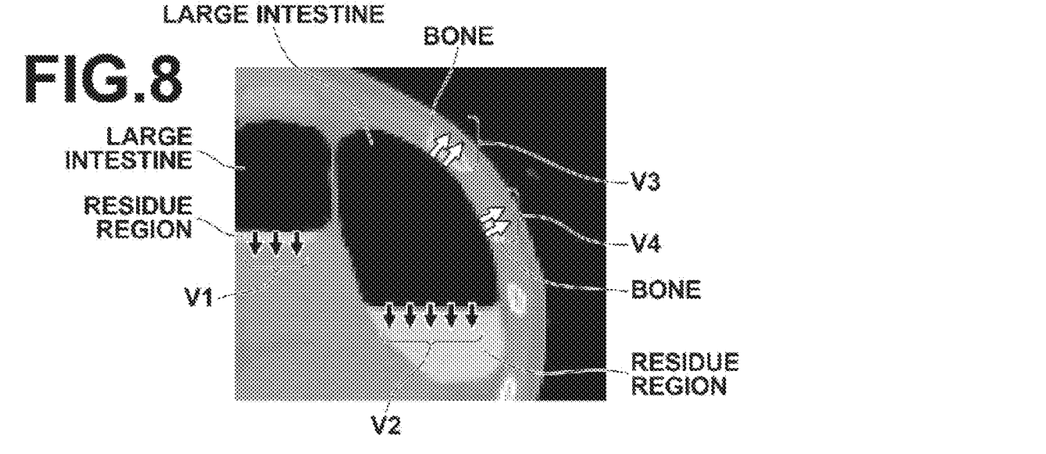
FIG. 8 shows an example of components in the normal direction of each voxel in a boundary candidate region.
Figure 9:
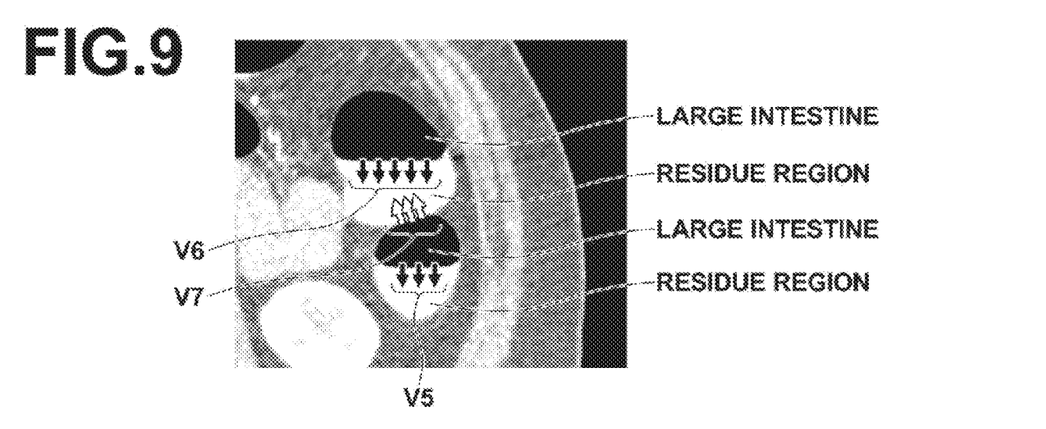
FIG. 9 shows an example of components in the normal direction of each voxel in a boundary candidate region.

FIGS. 8 and 9, each show an example of a normal direction component of each voxel in the boundary candidate regions. As the normal direction components V1 and V2 in FIG. 8 correspond to the representative direction component, the voxel groups having the normal direction components V1 and V2 are detected as boundary regions. On the other hand, the normal direction components V3 and V4 in FIG. 8 do not correspond to the representative direction component, and the voxel groups having the normal direction components V3 and V4 are not detected as boundary regions. Thus, a boundary candidate region that includes a bone region may be excluded from the boundary candidate regions.

The normal direction components V5 and V6 shown in FIG. 9 correspond to the representative direction component and the voxel groups having the normal direction components V5 and V6 are detected as boundary regions. On the other hand, the normal direction component V7 does not correspond to the representative direction component and the voxel group having the normal direction component V7 is not detected as a boundary region. This may avoid an erroneous detection in which a boundary candidate region that includes a boundary where portions of the large intestine are in contact with each other is detected as a boundary region.

Then, the residue region extraction unit 16 extracts a residue candidate region that includes a boundary region detected by the boundary region detection unit 15 in the manner described above as a residue region (S26).

The residue region elimination unit 17 eliminates voxels of the residue region from the three-dimensional image 5 based on information of the residue region detected by the residue region extraction unit 16, thereby obtaining a three-dimensional image 5 subjected to digital cleansing (S28).

The three-dimensional image 5 subjected to the digital cleansing in the residue region elimination unit 17 is outputted to the virtual endoscopic image generation unit 18, and the virtual endoscopic image generation unit 18 generates a virtual endoscopic image using the digital cleansed three-dimensional image 5 (S30).

The virtual endoscopic image generated by the virtual endoscopic image generation unit 18 is outputted to the display control unit 19, and the display control unit 19 displays the inputted virtual endoscopic image on the display 3 (S30).

According to the medical image diagnosis support system according to the foregoing embodiment, voting on directional components in the images of boundary candidate regions is performed, then a boundary region that includes the boundary between a gaseous region and a residue region is detected based on the voting result, and a residue candidate region that includes the boundary region is extracted as a residue region. This allows only a residue region without a bone and a contrasted blood vessel to be extracted with high accuracy. Further, an erroneous detection in which a boundary candidate region that includes a boundary where portions of the large intestine are in contact with each other is detected as a boundary region may be avoided. If the maximum peak is less than the threshold value in the polar coordinate space in S20 (S20, NO), a determination is made that no residue region is present, and the foregoing boundary region detection process, the residue region extraction process, and the residue region elimination process are not performed. That is, the three-dimensional image 5 obtained by the three-dimensional image obtaining unit 10 is directly outputted to the virtual endoscopic image generation unit 18, and a virtual endoscopic image is generated using the three-dimensional image 5.

In this way, if no residue region is present, the processing time to display the virtual endoscopic image may be reduced by omitting the boundary region detection process to the residue region elimination process.

In the foregoing embodiment, a boundary candidate region that includes a voxel group having maximum peak normal direction components less than 80% is preferably not detected as a boundary region. This may prevent an erroneous detection in which a boundary candidate region that includes only a few voxels having maximum peak normal direction components is detected as a boundary region. Further, not limited to the method described above and, for example, from the distribution state of a voxel group having maximum peak normal direction components, the plane direction thereof may be calculated, then a determination may be made whether or not the plane direction and the normal direction components are orthogonal, and a boundary candidate region determined to be orthogonal may be detected as a boundary region.

Further, in the foregoing embodiment, the voting process is performed by allocating one vote to the normal direction component of each pixel, but a weighted voting process may be performed. For example, the distance of each pixel from the body axis may be obtained and the weighted voting process may be performed such that the greater the distance, the smaller the weight.

Further, in the foregoing embodiment, the representative direction component is obtained by the voting process, but not limited to this, and, for example, a normal direction component vector of each pixel may be weight-added to obtain the representative direction component vector, or an average vector of a normal direction component vector of each pixel may be calculate and the average vector may be used as the representative direction component vector. The weighting method of the weighted addition described above is identical to that of the weighted voting process described above.

What is claimed is:

1. A region extraction processing apparatus, comprising:
    a gaseous region extraction unit that extracts a gaseous region from a lumen image that includes a hollow organ;
    a residue candidate region extraction unit that extracts a candidate of a residue region in the hollow organ from the lumen image as a residue candidate region;
    a boundary candidate region detection unit that detects a plurality of boundary candidate regions that include a boundary between the gaseous region and the residue candidate region;
    a representative direction component obtaining unit that obtains a representative direction component representing a plurality of directional components of an image in the boundary candidate regions;
    a boundary region detection unit that detects a boundary region that includes a boundary between the gaseous region and the residue region from the boundary candidate regions based on the representative direction component; and
    a residue region extraction unit that extracts the residue candidate region that includes the boundary region as the residue region.

2. The region extraction processing apparatus of claim 1, wherein the boundary candidate detection unit dilates each of the gaseous region and the residue candidate region and detects a region common to the gaseous region and the residue candidate region after the dilation as the boundary candidate region.

3. The region extraction processing apparatus of claim 1, wherein the representative direction component obtained unit obtains the representative direction component by performing a voting process on the plurality of directional components.

4. The region extraction processing apparatus of claim 3, wherein:
    the representative direction obtaining unit performs voting on values obtained by polar coordinate transformation of the directional components and obtains a directional component having a maximum peak in the polar coordinate space as the representative directional component; and
    the boundary region detection unit detects the boundary candidate region that includes the representative directional component as the boundary region.

5. The region extraction processing apparatus of claim 4, wherein, as a result of the voting, if the maximum peak is less than a predetermined threshold value, the detection of the boundary region in the boundary region detection unit and the extraction of the residue region in the residue region extraction unit are not performed.

6. The region extraction processing apparatus of claim 1, wherein the representative direction component obtaining unit calculates a normal direction component of each pixel in the boundary candidate region and obtains the representative direction component based on the normal direction component.

7. The region extraction processing apparatus of claim 6, wherein the representative direction component obtaining unit calculates the normal direction component of each pixel based on a density gradient in the boundary candidate region.

8. The region extraction processing apparatus of claim 7, wherein the representative direction component obtaining unit calculates the density gradient using a Sobel filter.

9. The region extraction processing apparatus of claim 1, wherein the residue candidate region extraction unit extracts a bone region or a contrasted blood vessel region along with the residue region as the residue candidate region.

10. The region extraction processing apparatus of claim 1, wherein the hollow organ is a large intestine.

11. The region extraction processing apparatus of claim 1, wherein the lumen image is a three-dimensional image.

12. A region extraction processing method, comprising the steps of:
    extracting a gaseous region from a lumen image that includes a hollow organ;
    extracting a candidate of a residue region in the hollow organ from the lumen image as a residue candidate region;
    detecting a boundary candidate regions that include a boundary between the gaseous region and the residue candidate region;
    obtaining a representative direction component representing a plurality of directional components of an image in the boundary candidate regions, and detecting a boundary region that includes a boundary between the gaseous region and the residue region from the boundary candidate regions based on the representative direction component; and
    extracting the residue candidate region that includes the boundary region as the residue region.

13. A non-transitory computer-readable recording medium containing a region extraction processing program that causes a computer to function as:
    a gaseous region extraction unit that extracts a gaseous region from a lumen image that includes a hollow organ;
    a residue candidate region extraction unit that extracts a candidate of a residue region in the hollow organ from the lumen image as a residue candidate region;
    a boundary candidate region detection unit that detects a plurality of candidate regions that include a boundary between the gaseous region and the residue candidate region;
    a representative direction component obtaining unit that obtains a representative direction component representing a plurality of directional components of an image in the boundary candidate regions;
    a boundary region detection unit that detects a boundary region that includes a boundary between the gaseous region and the residue region from the boundary candidate regions based on the representative direction component; and
    a residue region extraction unit that extracts the residue candidate region that includes the boundary region as the residue region.

14. A region extracting processing apparatus as defined in claim 1, wherein:
    the boundary region detection unit detects a boundary candidate region which includes the representative direction component as the boundary region.

15. A region extraction processing apparatus, comprising:
    a memory configured to store commands to be executed by a computer therein; and
    a processor;
    the processor being configured to execute the processes of:
        extracting a gaseous region from a lumen image that includes a hollow organ;
        extracting a candidate of a residue region in the hollow organ from the lumen image as a residue candidate region;
        detecting a plurality of boundary candidate regions that include a boundary between the gaseous region and the residue candidate region;
        obtaining a representative direction component representing a plurality of directional components of an image in the boundary candidate regions;
        detecting a boundary region that includes a boundary between the gaseous region and the residue region from the boundary candidate regions based on the representative direction component; and
        extracting the residue candidate region that includes the boundary region as the residue region.

* * * * *